United States Patent [19]

Nisolle

[11] 3,937,059
[45] Feb. 10, 1976

[54] DEVICE FOR MEASURING THE CONDENSATION TEMPERATURE OF A GAS OR A VAPOR

[75] Inventor: René Nisolle, Braine-Le-Compte, Belgium

[73] Assignee: Solvay & Cie., Brussels, Belgium

[22] Filed: May 17, 1974

[21] Appl. No.: 471,174

[30] Foreign Application Priority Data
May 23, 1973  France ................................. 73.18828

[52] U.S. Cl. ............................................... 73/17 A
[51] Int. Cl.² .......................................... G01N 25/68
[58] Field of Search .......... 73/17 A, 29, 335, 336.5; 340/235

[56] References Cited
UNITED STATES PATENTS

| | | | |
|---|---|---|---|
| 2,979,950 | 4/1961 | Leone | 73/17 |
| 3,083,565 | 4/1963 | Jennings | 73/17 |
| 3,284,003 | 11/1966 | Clemochowski | 73/17 |
| 3,416,356 | 12/1968 | Bridgeman | 73/17 |
| 3,552,186 | 1/1971 | Sproul | 73/17 |
| 3,780,564 | 12/1973 | Levina et al. | 73/17 |

OTHER PUBLICATIONS

Foldvari et al., "Capacitive Transducer" in "Instruments and Control Systems," Nov. 1964.

Primary Examiner—Herbert Goldstein
Attorney, Agent, or Firm—Spencer & Kaye

[57] ABSTRACT

A system for measuring the condensation temperature of a vapor or a gas composed of a capacitor whose plates are separated to define a space for receiving such vapor or gas, means for cooling, and measuring the temperature of the surface of one of the plates which bounds the space, and means for measuring the capacitance of the capacitor and for determining the temperature of the plate surface when such capacitance experiences a predetermined variation corresponding to the temperature at which condensate forms on such surface.

6 Claims, 2 Drawing Figures

DEVICE FOR MEASURING THE CONDENSATION TEMPERATURE OF A GAS OR A VAPOR

BACKGROUND OF THE INVENTION

The present invention relates to a device for measuring the condensation temperature of an organic or inorganic gas or vapor by means of an electric capacitor.

The known devices for measuring condensation points, which are disclosed, for example, in the text, A. Wexler, *Humidity and Moisture* — Rheinhold Publ. Corp. N.Y. — Chapman and Hall Ltd. — London (1965), generally include a mirror equipped with a thermocouple. The mirror can be cooled and the formation of the condensate is observed with the naked eye or with the help of any apparatus which makes this detection possible, for example a photoelectric cell. The temperature measured during the formation of the condensate can be maintained by alternate heating and cooling processes which have an instantaneous action and are adjusted as finely as possible so as to attain a temperature which differs from the actual condensation temperature by only a few hundredths of a degree. However, these devices possess the disadvantages characteristic of all optical measurements, that is to say they are easily soiled, they lack robustness, their optical path is difficult to align, and the like. The devices of this type require frequent maintenance and it is difficult to adapt them to industrial processes which are carried out continuously. In these cases, it is thus necessary to use measuring and regulating apparatuses based on different principles, which are more robust but also slower and more expensive and which function discontinuously, amongst which are gas chromatography apparatuses.

SUMMARY OF THE INVENTION

It is an object of the present invention to overcome the disadvantages of the conventional regulating apparatuses, for example, the chromatograph and the like, as well as those of the apparatuses for measuring the condensation temperature by means of a cooled mirror.

These and othe objects of the invention are achieved by a device capable of obtaining a measure of the condensation temperature of an organic or inorganic gas or vapor and composed of two plates which are insulated electrically from one another and which are in contact with the gas or the vapor, one of these plates being preferably a grid and the other, which possesses a surface on which the condensate is deposited under appropriate conditions, being equipped with cooling and optionally, heating means and with a temperature recording device positioned as close as possible to this surface, these insulated plates forming an electric capacitor having a given capacitance when the space which separates them is occupied by a gas and having a markedly different capacitance when a condensate is deposited on one of the plates. The device further includes a member for measuring the capacitance of this capacitor and for detecting a predetermined variation in this capacitance, the temperature to be measured being that given by the temperature measuring device at the instant when this capacitance variation is detected.

In order to measure a condensation temperature of a gas or a vapor by means of the device which is the subject of the invention, the cooling means is employed; the temperature of the receiving plate falls, as does that of the vapor in contact with this surface, so that, at the instant when the condensation temperature is reached, a liquid film forms on this surface. This phenomenon is accompanied by a sudden change in the capacitance of the capacitor formed by the two plates, and this change is detected by means of a capacitance measuring bridge, which can be of any type provided that it is sufficiently accurate, for example, the Wayne-Kerr B 642 type measuring bridge.

The temperature of the plate in question, measured at the instant when the capacitance changes, is the condensation temperature of the vapor.

This measurement, which can be used directly, nevertheless presents a slight error due to the evolution of heat which accompanies the condensation of a vapor, i.e., the latent heat of condensation. In order to eliminate this error, it is possible to incorporate into the cooling circuit a temperature regulator which is controlled by the capacitance measuring bridge and whose function is to establish and maintain a temperature which ensures that the capacitor has a given capacitance which lies within the range within which the capacitance of the capacitor varies during the formation of a condensate. A value for the temperature is thus obtained which differs from the actual condensation temperature by only a few tenths of a degree.

Widely diverse materials can be employed for the grid and the receiving surface, and, in fact, it is sufficient if the materials are good conductors of electricity. The meshes of the grid can have diverse dimensions and, in fact, only serve to allow the gases or vapors to circulate freely between the plates of the capacitor.

The means for cooling the receiving plate is chosen on the basis of the range of temperatures to be measured. It can be a cold gas or liquid or an electric, magnetic or electromagnetic cooling system for example based on the Peltier effect.

The receiving plate can also be equipped with a heating means which makes it possible to make the measurement more accurate by repetition; the plate is heated until the condensate disappears and the capacitance returns to its original value, and then the plate is cooled again.

The temperature detector can be chosen from the entire range of existing apparatuses, but in more or less complex installations, the measuring device is obviously selected so that it can be connected to an instrument which records this temperature continuously and-/or to influence parameters of the industrial process which it is desired to control, so as to effect optimum automatic control; for example, a polymerization chain regulation can be controlled from the measurement of the condensation temperature of a monomer.

The device which forms the subject of the invention makes it possible to measure very diverse condensation temperatures, no matter what the existing pressure may be, and in particular at pressures above atmospheric pressure and even relatively high pressures.

Moreover, because of its reliability and its robustness, the device makes it possible to control various industrial processes.

This control is effected by means of various accessories which can convert the electrical current, which is a function of the value of the condensation temperature, into a control signal which acts either on a pressure, a temperature, a flow rate or a concentration of the process.

More particularly, the device can be used for controlling the above-mentioned parameters of gas phase polymerization processes, for example for controlling the concentration or partial pressure of monomers.

DESCRIPTION OF THE PREFERRED EMBODIMENTS

Figure 1:
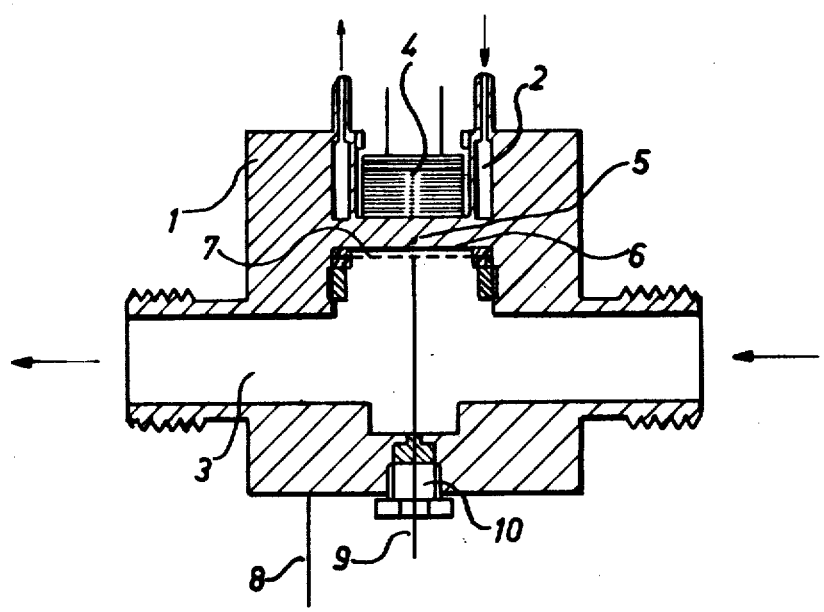
FIG. 1 is a cross-sectional view of one preferred embodiment of a capacitive unit according to the present invention.

The device shown in FIG. 1 consists of various parts including a cell body 1 made of a material which is a very good conductor of heat and electricity at least at the level of the cooled surface 6, which body can be connected to the gas circuit of the installation in question by any means whatsoever, for example screw threads, and in which a network has been provided through which a cooling agent 2 can flow. This cell body is equipped with an opening 3 which passes right through it so as to allow the gases and vapors to be examined to flow freely, and possesses, in the immediate vicinity of the network through which the cooling agent flows, the cooled smooth surface 6 where the condensate will form. The device further includes a heating resistance 4 in intimate contact with the cell body 1 so as to provide rapid and effective heating, a temperature measuring apparatus 5 mounted in the cell body 1 and placed as close as possible to the cold surface 6 on which the condensate is deposited, and a grid 7 which is a good conductor of electricity mounted in such a way as to be perfectly insulated from body 1 and positioned opposite the wall 6 of the cell body 1 and at a distance of a few tenths of a millimeter from the latter, the grid, together with this wall, forming a capacitor having a well-defined capacitance in vacuo. The grid 7 is designed in such a way as to allow the gases and vapors to flow freely between the plates of the capacitor.

Figure 2:
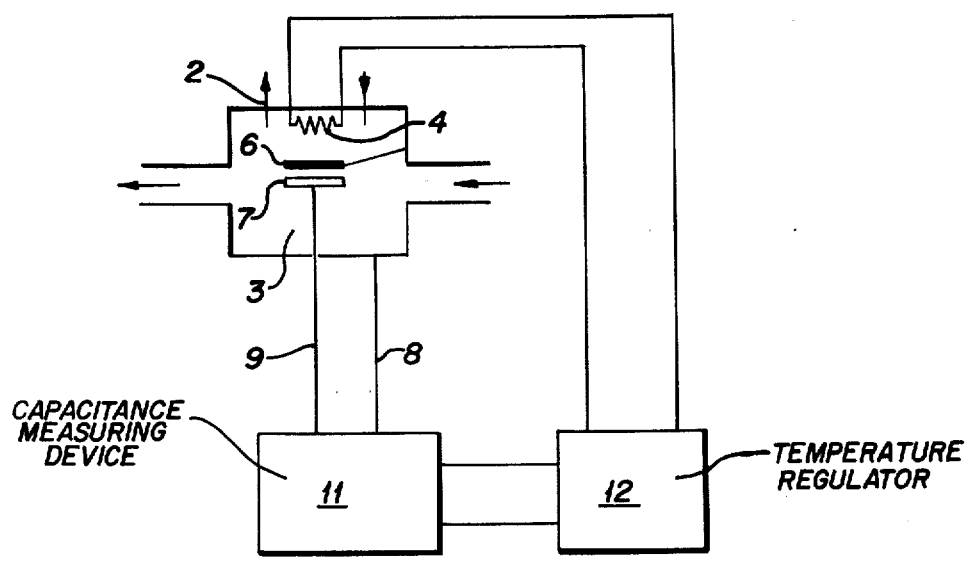
FIG. 2 is a schematic view of one embodiment of condensation temperature measuring system according to the invention.

The grid 7 and the cell body 1 are connected by means of leads 8 and 9, to a capacitance measuring bridge 11 illustrated diagramatically in FIG. 2. The lead 9 connecting the grid 7 is insulated from the cell body 1 by means of an assembly using a stuffing-box 10 packed with insulating material.

The capacitance of the capacitor formed by the cold wall 6 and the grid 7 is a function of the surface areas thereof, the distance between them, and the dielectric present therebetween.

This capacitance $C_0$ has a reference value of 20pF in vacuo for the assembly in question. In the majority of cases, this capacitance is practically constant and identical to the value $C_0$ for as long as gases or vapors are present.

In any case, if this did not apply, the capacitance of the capacitor in the presence of the gas or the vapor would be well defined and measurable. However, if the dielectric between the plates of the capacitor consists of a liquid, the capacitance changes and becomes: $C_0 \times \epsilon_{liq}$ wherein $\epsilon_{liq}$ is the relative dielectric constant of the liquid considered and is generally between 2 and 120.

When the plate 6 is being cooled in the presence of a vapor or a gas, the appearance of liquid thus manifests itself by an instantaneous change in the capacitance of the capacitor. It was, however, shown during tests that the capacitor itself was, due to physical imperfections, subject to variations and that its actual capacitance varied within certain limits as a function of the temperature and the pressure. In order to overcome this disadvantage, the limits of this variation in capacitance were investigated in preliminary tests, and a critical value for the capacitance, higher than the limit of the variations recorded, that is to say 25 pF in our example, was fixed, this being a critical capacitance for which it is certain that a liquid film of minimum thickness will have been formed.

The condensation point can consequently be measured by cooling the cell body gradually and by measuring the temperature corresponding to a value of 25 pF for the capacitance of the capacitor. This measurement can however be made much more precisely by incorporating into the circuit, as shown in FIG. 2, a temperature regulator 12 which acts on the supply of heat to the cell body 1, controls the temperature of the wall 6 as finely as possible, and has the function of regulating the heating so as to maintain a constant capacitance of 25 pF for the capacitor.

The temperature measuring device 5 makes it possible to record, during the entire experiment, and preferably automatically, the temperature of the wall 6 corresponding to the chosen capacitance (25 pF). In order to avoid errors due to temperature gradients, it is obvious that it is of value to assemble the apparatus so that the temperature recording device 5 is as close as possible to the wall 6. The temperature recording is now in the form of a succession of damped oscillations, the average value of which represents, to within a few tenths of a degree, the value of the condensation temperature of the gas or vapor considered.

The condensation temperatures which can be measured are not limited in any way, either with respect to low temperatures or with respect to high temperatures. It suffices to use suitable heating and cooling systems and agents such as cold gases and liquids and electric, magnetic or electromagnetic systems which make it possible to achieve the desired temperatures. Furthermore, there is not any limitation, either, as to the nature of the organic or inorganic gas or vapor, whose condensation temperature it is desired to measure. In fact, the value of $\epsilon_{liq}$ is always sufficiently great relative to $\epsilon_{gas}$ to allow measurements to be taken. It is however obvious, that the larger the ratio $\epsilon_{liq}/\epsilon_{gas}$ and the larger $\epsilon_{liq}$, the easier and more precise the measurements.

It will be understood that the above description of the present invention is susceptible to various modifications, changes and adaptations, and the same are intended to be comprehended within the meaning and range of equivalents of the appended claims.

I claim:

1. Device for measuring the condensation temperature of an organic or inorganic vapor or gas, comprising two electrically conductive plates insulated electrically from one another and spatially separated from one another by a space free of any solid material and arranged to contain such gas or vapor, one of said plates presenting a surface on which a condensate of such gas or vapor is deposited under appropriate conditions; cooling means operatively associated for cooling said surface through a temperature range containing the temperature at which such gas or vapor will begin to condense; a temperature measuring device positioned as close as possible to said surface for providing an indication of the temperature of said surface; said insulated plates forming an electric capacitor of a given capacitance when the space which separates them is occupied by a vapor or gas and of a markedly different capacitance when a condensate is deposited on said one of said plates; and a device for measuring the capacitance of said capacitor and detecting a predetermined variation in this capacitance, the temperature to be measured being that given by said temperature measuring device at the instant when this variation is detected.

2. Device as defined in claim 1 wherein the other of said plates is porous to the gas or vapor.

3. Device as defined in claim 2 wherein the other of said plates is in the form of a grid.

4. A device as defined in claim 1 further comprising heating means operatively associated with said surface.

5. Device as defined in claim 1 further comprising a temperature regulator, controlled by said capacitance measuring device for establishing and maintaining a temperature which ensures that said capacitor has a given capacitance which lies within the range within which the capacitance of said capacitor varies during the formation of a condensate.

6. Device as defined in claim 5 wherein said capacitance measuring device is a capacitance measuring bridge.

* * * * *